United States Patent
Wingen et al.

(10) Patent No.: US 6,231,786 B1
(45) Date of Patent: May 15, 2001

(54) FLUORINATED AZOLES, AND THEIR USE IN LIQUID-CRYSTALLINE MIXTURES

(75) Inventors: Rainer Wingen, Hattersheim; Barbara Hornung, Hasselroth, both of (DE); Ayako Ogawa, Kakegawa (JP); Wolfgang Schmidt, Köln (DE)

(73) Assignee: Clariant GmbH, Frankfurt am Main (DE)

( * ) Notice: Subject to any disclaimer, the term of this patent is extended or adjusted under 35 U.S.C. 154(b) by 0 days.

(21) Appl. No.: 09/484,680

(22) Filed: Jan. 18, 2000

(30) Foreign Application Priority Data

Jan. 19, 1999 (DE) ................................. 199 01 890
Apr. 8, 1999 (DE) ............................. 199 15 864

(51) Int. Cl.⁷ ..................... C09K 19/34; C09K 19/02; C07D 217/00; C07D 211/56
(52) U.S. Cl. ................... 252/299.61; 546/146; 546/200; 546/202; 546/225; 546/230; 546/215; 556/405; 548/237
(58) Field of Search ........... 252/299.61; 546/146, 546/200, 202, 215, 237, 225, 230; 548/237; 556/405

(56) References Cited

U.S. PATENT DOCUMENTS

| | | | |
|---|---|---|---|
| 5,076,961 | 12/1991 | Nakamura et al. | 252/299.61 |
| 5,200,109 | 4/1993 | Iwaki et al. | 252/299.61 |
| 5,262,083 | * 11/1993 | Mori et al. | 252/299.61 |
| 5,595,685 | * 1/1997 | Takiguchi et al. | 252/299.61 |
| 5,658,492 | * 8/1997 | Murashiro et al. | 252/299.61 |
| 5,695,683 | * 12/1997 | Takeichi et al. | 252/299.61 |
| 5,708,819 | * 1/1998 | Yamashita et al. | 252/299.61 |

FOREIGN PATENT DOCUMENTS

| | | |
|---|---|---|
| 197 48 432 | 5/1999 | (DE) . |
| 0032362 | 7/1981 | (EP) . |
| 0309514 | 4/1989 | (EP) . |
| 0335348 | 10/1989 | (EP) . |
| 0439170 | 7/1991 | (EP) . |

* cited by examiner

*Primary Examiner*—C. H. Kelly
(74) *Attorney, Agent, or Firm*—Frommer Lawrence & Haug LLP

(57) ABSTRACT

In the fluorinated azoles of the formula (I)

$$R^1(-A^1)_a-T-(A^2-)_b(M-A^3-)_cR^2 \qquad (I)$$

the symbols and indices have -the following meanings:
  T is undirected and is
    4-fluorothiazole-2,5-diyl, 5-fluorothiazole-2,4-diyl, 4-fluorooxazole-2,5-diyl, 5-fluorooxazole-2,4-diyl or 4-fluoroisoxazole-2,5-diyl;
  $R^1$ and $R^2$ are identical or different and are
    hydrogen or a straight-chain or branched $C_{1-20}$-alkyl or $C_{2-20}$-alkenyl radical (with or without asymmetrical carbon atoms);
  $A^1$, $A^2$ and $A^3$ are identical or different and are, for example,
    phenylene-1,4-diyl or cyclohexane-1,4-diyl;
  M is undirected and is
    $-OC(=O)-$, $-OCH_2-$, $-CH_2CH_2-$, $-OC(=O)CH_2CH_2-$, $-OCH_2CH_2CH_2-$, $-C \equiv C-$, $-CH_2CH_2CH_2CH_2-$ or a single bond;
  a, b and c, independently of one another, are 0 or 1, with the proviso that the sum a+b+c is 1 or 2.

8 Claims, No Drawings

FLUORINATED AZOLES, AND THEIR USE IN LIQUID-CRYSTALLINE MIXTURES

Besides nematic and cholesteric liquid crystals, optically active, tilted, smectic (ferroelectric) liquid crystals have also recently been used in commercial display devices.

Clark and Lagerwall have been able to show that the use of ferroelectric liquid crystals (FLCs) in very thin cells results in opto-electrical switching or display elements which have response times which are faster by a factor of up to 1000 compared with conventional TN ("twisted nematic") cells (see, for example, EP-A 0 032 362). Owing to this and other favorable properties, for example the possibility of bistable switching and the virtually viewing angle-independent contrast, FLCs are basically highly suitable for areas of application such as computer displays.

For a more detailed explanation of the technical requirements of FLCs, see European Patent Application 97118671.3 and DE-A 197 48 432.

Azole derivatives have already been described for use in liquid-crystal mixtures: thiadiazole derivatives, for example in EP-A 0 309 514, EP-A 0 335 348, U.S. Pat. No. 5,076,961, U.S. Pat. No. 5,200,109; 1,3-thiazole derivatives, for example in EP-A 0 309 514, EP-A 0 439 170; benzothiazole derivatives, for example in JP-A 09-059266, isoxazoles, for example in JP-A 10-333113.

However, since the development, in particular of ferroelectric liquid-crystal mixtures, can in no way be regarded as complete, the manufacturers of displays are interested in a very wide variety of components for mixtures, partly because only the interaction of the liquid-crystalline mixtures with the individual components of the display device or of the cells (for example the alignment layer) allows conclusions to be drawn on the quality of the liquid crystalline mixtures too.

Surprisingly, it has now been found that fluorinated azoles of the formula (I), even when admixed in small amounts, have a favorable effect on the properties of liquid-crystal mixtures, in particular chiral smectic mixtures, for example regarding the dielectric anisotropy and/or the melting point, but also regarding the switching behavior.

The invention therefore relates to fluorinated azoles of the formula (I)

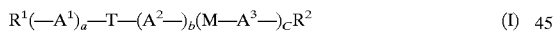

where the symbols and indices have the following meanings:

T is undirected and is
  4-fluorothiazole-2,5-diyl, 5-fluorothiazole-2,4-diyl, 4-fluorooxazole-2,5-diyl, 5-fluorooxazole-2,4-diyl or 4-fluoroisoxazole-2,5-diyl;

$R^1$ and $R^2$ are identical or different and are
  hydrogen or a straight-chain or branched $C_{1-20}$-alkyl or $C_{2-20}$-alkenyl radical (with or without asymmetrical carbon atoms), where
  a) one or two nonterminal $CH_2$ groups may be replaced by —O— and/or —C(=O)—, with the proviso that two adjacent $CH_2$ groups cannot be replaced by heteroatoms, and/or
  b) one or more $CH_2$ groups may be replaced by —CH=CH— and/or —C≡C—, and/or
  c) one $CH_2$ group may be replaced by —Si(CH$_3$)$_2$—, cyclopropane-1,2-diyl, cyclobutane-1,3-diyl, cyclopentane-1,4-diyl, bicyclo[1.1.1]pentane-1,3-diyl or cyclohexane-1,4-diyl, and/or
  d) one or more H atoms may be replaced by F and/or CN;
  e) in the case of a straight-chain or branched alkyl radical containing asymmetrical carbon atoms, the asymmetrical carbon atoms either have —CH$_3$, —OCH$_3$, —CF$_3$, F, CN and/or $C_1$ as substituents, or are incorporated into a 3- to 7-membered ring, in which, in addition, one or two non-adjacent $CH_2$ groups may be replaced by —O— and one $CH_2$ group may be replaced by —OC(=O)—;

$A^1$, $A^2$ and $A^3$ are identical or different and are
  phenylene-1,4- diyl, unsubstituted or monosubstituted or disubstituted by CN or F, phenylene-1,3-diyl, unsubstituted or monosubstituted or disubstituted by CN or F, cyclohexane-1,4diyl, in which one or two H atoms may be replaced by CN and/or CH$_3$ and/or F, 1-cyclohexene-1,4-diyl, in which one H atom may be replaced by F, 1-alkyl-1silacyclohexane-1,4-diyl, pyridine-2,5-diyl, unsubstituted or monosubstituted by F, pyrimidine-2,5-diyl, unsubstituted or monosubstituted by F, or thiophene-2,5-diyl;

M is undirected and is
  —OC(=O)—, —OCH$_2$—, —CH$_2$CH$_2$—, —OC(=O) CH$_2$CH$_2$—, —OCH$_2$CH$_2$CH$_2$—, —C≡C—, —CH$_2$CH$_2$CH$_2$CH$_2$— or a single bond;

a, b and c, independently of one another, are 0 or 1, with the proviso that the sum a+b+c is 1 or 2.

For example, b+1, and a+c is at least 1.

According to an embodiment of the invention, $R^1$ and $R^2$ cannot be alkenyl radicals or, with the above provisos e), straight-chain alkyl radicals.

For use in liquid-crystal mixtures, preference is given to the following compounds of the formulae (I-1) to (I-9):

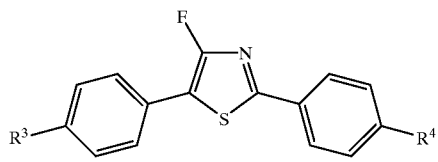

(I-1)

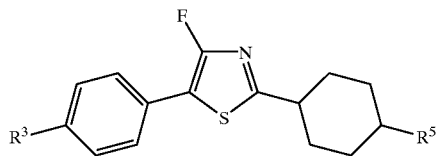

(I-2)

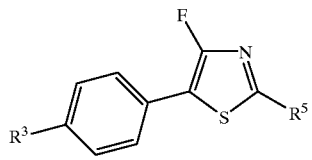

(I-3)

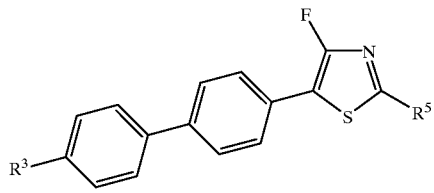

(I-4)

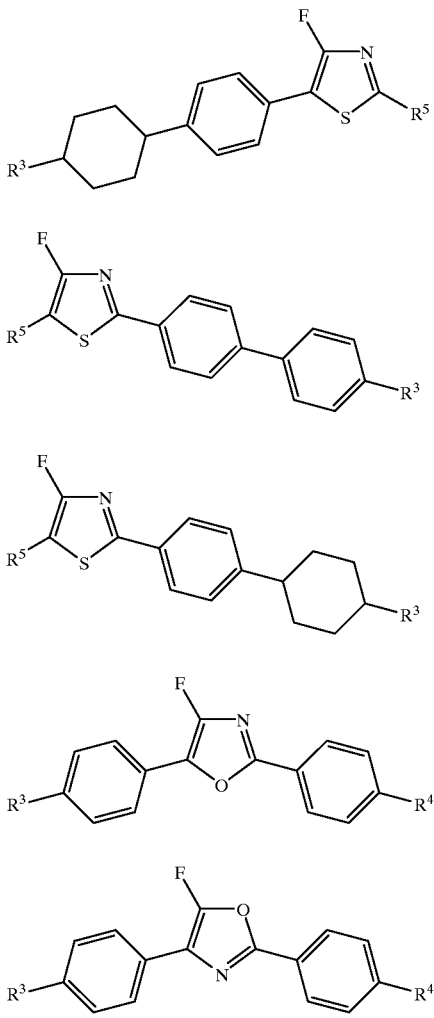

in which:
R³ and R⁴, independently of one another, are hydrogen or a straight-chain or branched alkyl radical (with or without asymmetrical carbon atoms) having 1 to 16 carbon atoms, in which, in addition, one nonterminal CH₂ group may be replaced by —O— or, undirected, —OC(=O)— and in which one or more H atoms may be replaced by F;

R⁵ is hydrogen or a straight-chain or branched alkyl radical (with or without asymmetrical carbon atoms) having 1 to 16 carbon atoms, in which, in addition, one nonterminal CH₂ group which is not directly adjacent to the ring may be replaced by —O— or, undirected, —OC(=O)— and in which one or more H atoms may be replaced by F.

Particular preference is given to the compounds of the formula (I-1) in which R³ and R⁴ are a straight-chain alkyl radical having 2 to 12 carbon atoms.

Particular preference is likewise given to the compounds of the formula (I-1) in which R³ or R⁴ is hydrogen and the other radical R³ or R⁴ is a straight-chain alkyl or alkoxy radical having 2 to 12 carbon atoms.

Particular preference is likewise given to the compounds of the formula (I-1) in which R³ or R⁴ is a straight-chain alkyl radical having 2 to 12 carbon atoms and the other radical R³ or R⁴ is a straight-chain alkoxy radical having 2 to 12 carbon atoms.

Particular preference is likewise given to the compounds of the formula (I-1) in which R³ or R⁴ is an alkanoyloxy radical having 2 to 12 carbon atoms and the other radical is an alkyl radical having 1 to 12 carbon atoms.

Particular preference is likewise given to the compounds of the formula (I-2) in which R³ is a straight-chain alkyl or alkoxy radical having 2 to 12 carbon atoms and R⁵ is hydrogen or a straight-chain alkyl radical having 1 to 12 carbon atoms.

Particular preference is likewise given to the compounds of the formula (I-8) in which R³ and R⁴ are straight-chain alkyl or alkoxy radicals having 1 to 12 carbon atoms.

Particular preference is likewise given to the compounds of the formula (I-9) in which R³ and R⁴ are straight-chain alkyl or alkoxy radicals having 1 to 12 carbon atoms.

Of the compounds of the formula (I) which are to be used as optically active components (dopants), preference is given to those containing the following groups:

a) —C*H(CH₃)C$_m$H$_{2m+1}$, where m has a value of from 2 to 8
b) —OC*H(CH₃)C$_m$H$_{2m+1}$, where m has a value of from 2 to 8
c) —OC*H(CH₃)CO₂C$_m$H$_{2m+1}$, where m has a value of from 1 to 10
d) —OC(=O)C*H(CH₃)OC$_m$H$_{2m+1}$, where m has a value of from 1 to 10
e) —OC(=O)C*H(F)C$_m$H$_{2m+1}$, where m has a value of from 1 to 10
f) —OCH₂C*H(F)C$_m$H$_{2m+1}$, where m has a value of from 1 to 10
g) —OCH₂C*H(F)C*H(F)C$_m$H$_{2m+1}$, where m has a value of from 1 to 10 in which C* denotes the asymmetrical carbon atom.

The compounds of the formula (I) can also be employed for the production of medicaments/pharmaceuticals and crop-protection products/agrochemicals.

For use as a component of agrochemicals or pharmaceuticals or alternatively as an intermediate in the production of agrochemicals or pharmaceuticals, preference is given to the compounds of the formula (I) in which
T, A², R¹ and R² are as defined above, and
a and c are each zero.

Particular preference is given in this context to the compounds in which T is 4-fluorothiazole-2,5-diyl or 4-fluorooxazole-2,5-diyl.

The compounds according to the invention are prepared by methods known per se from the literature, as described in standard works on the organic synthesis, for example Houben-Weyl, Methoden der organischen Chemie [Methods of Organic Chemistry], Georg-Thieme-Verlag, Stuttgart.

However, it may prove necessary to vary/modify the literature methods for the requirements of mesogenic units since, for example, functional derivatives having long (>C6) alkyl chains frequently exhibit a lower reaction capacity than, for example, the methyl or ethyl analogues.

In this connection, particular reference is made to the following references in which the synthesis of halogenated azole derivatives is described, but which do not reveal to the person skilled in the art a suitability of the fluorinated azoles according to the invention as components of liquid-crystalline mixtures:

Reference 1: Sakamoto et al., Synthesis 1992 (6), 552; Pd-catalyzed coupling reactions of haloazoles with C—H—acidic compounds [CAN 117:111526].

Reference 2: Herkes et al., J. Heterocycl. Chem. 13 (6), 1297 (1976); synthesis and reactions of perhalogenated thiazoles [CAN 86:106457].

Reference 3: Yamanaka et al., Heterocycles 31 (6), 1115 (1990); $S_N2$ reactions of halo-1,3-azoles [CAN 113:191253].

Reference 4: JP-A 63-250385; synthesis and reactions of perhalogenated azoles [CAN 111:153776].

Reference 5: U.S. Pat. Nos. 4,892,799 and 5,025,097 for the synthesis of 4-chlorooxazoles.

As far as the linking of functional derivatives of fluorinated azoles with other liquid crystal-specific units is concerned, express reference is made to DE-A 197 48 432, in which a list of methods customary to the person skilled in the art is given.

The invention also relates to the use of compounds of the formula (I) in liquid-crystal mixtures, preferably smectic and nematic liquid-crystal mixtures, particularly preferably ferroelectric liquid-crystal mixtures. Particular reference is given to use in ferroelectric liquid-crystal mixtures operated in inverse mode or in displays having active matrix elements; very particular preference is given to use in inverse mode liquid-crystal mixtures.

The invention furthermore relates to liquid-crystal mixtures, preferably smectic and nematic liquid-crystal mixtures, particularly preferably ferroelectric (chiral smectic) liquid-crystal mixtures which comprise one or more compounds of the formula (I).

The liquid-crystal mixtures according to the invention generally comprise from 2 to 35 components, preferably from 2 to 25 components, particularly preferably from 2 to 20 components.

They generally comprise from 0.01 to 80% by weight, preferably from 0.1 to 60% by weight, particularly preferably from 0.1 to 30% by weight, of one or more, preferably from 1 to 10, particularly preferably from 1 to 5, very particularly preferably from 1 to 3, compounds of the formula (I) according to the invention.

Further components of liquid-crystal mixtures which comprise compounds of the formula (I) according to the invention are preferably selected from known compounds having smectic and/or nematic and/or cholesteric phases. Further mixture components which are suitable in this context are listed, in particular, in international patent application PCT/EP 96/03154 and DE-A 197 48 432, which are expressly incorporated herein by way of reference.

The mixtures according to the invention can in turn be used in electro-optical or fully optical elements, for example display elements, switching elements, light modulators, elements for image processing and/or signal processing, or generally in the area of nonlinear optics.

The invention therefore furthermore relates to a switching and/or display device preferably containing a smectic liquid-crystal mixture which comprises one or more compounds of the formula (I).

Particular preference is given to ferroelectric switching and/or display devices operated in normal or inverse ($\tau V_{min}$) mode (see, for example, J. C. Jones, M. J. Towler, J. R. Hughes, Displays 1993, 14, No. 2, 86–93; M. Koden, Ferroelectrics 1996, 179, 121–129).

Particular preference is likewise given to ferroelectric switching and/or display devices containing active matrix elements (see, for example, DE-A 19822830).

The present application cites various documents, for example in order to illustrate the technical background to the invention. All these documents are expressly incorporated herein by way of reference.

The invention is illustrated in greater detail by the examples below without this being intended to represent a restriction thereto.

EXAMPLE 1

4-Fluoro-2-(4-hexylphenyl)5-(4-nonylphenyl)-1,3-thiazole

A solution of 4 g of F-TEDA-BF$_4$ [140681-55-6] in 90 ml of acetonitrile is added at 20° C. to a suspension of 5 g of 2-(4-hexylphenyl)-5-(4-nonylphenyl)-1,3-thiazole [139674-48-9] in 50 ml of acetonitrile, and the mixture is stirred at the same temperature for 24 hours. 700 ml of water are added, and the mixture is extracted twice with 100 ml of dichloromethane each time. The combined organic phases are dried and evaporated under reduced pressure. The residue is purified by chromatography (silica gel, heptane/ethyl acetate 20:1) and subsequently recrystallized (from acetonitrile).

The product has the characteristic signals in the $^1$H-NMR (400 MHz, CDCl$_3$) at δ=7.81 (d, 2H), 7.53 (d, 2H) and 7.25–7.2 (m, 4H) ppm and the characteristic signal in the $^{19}$F-NMR (376.5 MHz, CDCl$_3$/CFCl$_3$) at δ=−107 ppm. It has the following phases: X53N79I.

Compounds (I-1) to (I-7) can be prepared analogously.

EXAMPLE 2

4-Fluoro-2-(4-hexylphenyl)-5-(4-octyloxyphenyl)1,3-thiazole is obtained by the Mitsunobu reaction between 1-octanol and 4-fluoro-2-(4-hexylphenyl)-5-(4-hydroxyphenyl)-1,3-thiazole [obtained by ether cleavage (for example using hydrobromic acid/acetic acid or boron tribromide) of 4-fluoro-2-(4-hexylphenyl)-5-(4-methoxyphenyl)-1,3-thiazole, which is accessible as described in Example 1 from 2-(4-hexylphenyl)-5-(4-methoxyphenyl)-1,3-thiazole [72997-60-5].

From compounds (I-1), (I-2), (I-3), (I-4) and (I-6), the compounds in which, in $R^3$ or $R^3$ and $R^4$ (I-1), the CH$_2$ group adjacent to the ring has been replaced by —O— can be obtained analogously.

EXAMPLE 3

4-Fluoro-2-(4-hexylphenyl)-5-(4-octylcarbonyloxy) phenyl-1,3-thiazole is obtained by esterification of 4-fluoro-2-(4-hexylphenyl)-5-(4-hydroxyphenyl)-1,3-thiazole using nonanoic acid in the presence of DCC.

From compounds (I-1), (I-2), (I-3), (I-4) and (I-6), the compounds in which, in $R^3$ and $R^4$, the CH$_2$ group adjacent to the ring has been replaced by —OC(=O)— can be obtained analogously; furthermore the compounds of the formula (I) in which M is —OC(=O)— or —OC(=O) CH$_2$CH$_2$—.

The compounds of the formula (I) in which M=—OCH$_2$— or —OCH$_2$CH$_2$CH$_2$— can also be obtained analogously to Example 2 from the corresponding phenols.

After conversion of said phenols into esters of trifluoromethanesulfonic acid, compounds of the formula (I) in which M is —C≡C—, —CH$_2$CH$_2$—, —CH$_2$CH$_2$CH$_2$CH$_2$— or a single bond between two aromatic (including heteroaromatic) rings can also be obtained by coupling reactions (for example Suzuki reaction, Hagihara reaction or Heck coupling).

EXAMPLE 4

2-(4-Butylphenyl)-4-fluoro-5-(4methoxyphenyl)oxazole is prepared analogously to Example 1, but using 2-(4- butylphenyl)-5-(4-methoxyphenyl)oxazole (preparation analogous to EP-B 439 170 by cyclization of N-(4-butylbenzoyl)-(4-methoxy)phenacylamine using phosphorus pentoxide instead of phosphorus pentasulfide).

The product has the characteristic signals in the $^1$H-NMR (400 MHz, CDCl$_3$) at δ=7.97 (d, 2H), 7.62 (d, 2H), 7.22 (d, 2H), 6.93 (d, 2H), 3.80 (s, 3H), 2.63 (t, 2H) ppm and the characteristic signal in the $^{19}$F-NMR (376.5 MHz, CDCl$_3$/CFCl$_3$) at δ=−140 ppm; melting point: 72° C.

Further compounds of the formulae (I-8) and (I-9) can be obtained analogously thereto or analogously to Examples 1, 2 or 3.

EXAMPLE 5

A chiral smectic liquid-crystal mixture consisting of

| | |
|---|---|
| 2-cyclohexyl-5-(4-nonyloxyphenyl)-1,3,4-thiadiazole | 11.1% |
| 2-(4-ethoxyphenyl)-5-octyloxypyrimidine | 11.1% |
| 5-octyl-2-(4-octyloxyphenyl)pyrimidine | 14.7% |
| 5-octyloxy-2-(4-octyloxyphenyl)pyrimidine | 4.9% |
| 2-(4-decyloxyphenyl)-5-octylpyrimidine | 11.7% |
| 2-(4-hexyloxyphenyl)-5-octyloxypyrimidine | 9.9% |
| 2-(4-butoxyphenyl)-5-octyloxypyrimidine | 9.7% |
| 2-(4-decyloxyphenyl)-5-octyloxypyrimidine | 9.5% |
| 2-(4-hexyloxyphenyl)-5-octylpyrimidine) | 15.2% |
| 4-[4'-(S)-(2-fluorooctyloxy)biphenyl-4-yl]-1-heptyl-cyclohexanecarbonitrile | 2.2% | is mixed with in each case 10% of
  case A the comparative compound 2-(4-hexylphenyl)-5-(4-nonylphenyl)thiazole
  case B the compound according to the invention 4-fluoro-2-(4-hexylphenyl)-5-(4-nonylphenyl)thiazole.

In case A, a mixture is obtained which has an $S_c/S_A$ transition of 61° C. and a 2Θ of 14.7° (5 V) or 20.4° (10 V);
in case B, the mixture has a somewhat lower $S_c/S_A$ transition of 54° C. and a 2Θ of 17.7° (5 V) or 24.8° (10 V).

What is claimed is:

1. A fluorinated azole of the formula (I)

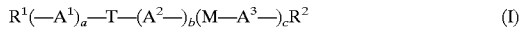

$$R^1(-A^1)_a-T-(A^2-)_b(M-A^3-)_cR^2 \quad (I)$$

where the symbols and indices have the following meanings:
T is undirected and is
  4-fluorothiazole-2,5-diyl, 5-fluorothiazole-2,4-diyl, 4-fluorooxazole-2,5-diyl, 5-fluorooxazole-2,4-diyl or 4-fluoroisoxazole-2,5-diyl;
$R^1$ and $R^2$ are identical or different and are
  hydrogen or a straight-chain or branched $C_{1-20}$-alkyl or $C_{2-20}$-alkenyl radical (with or without asymmetrical carbon atoms), where
  a) one or two nonterminal CH$_2$ groups may be replaced by —O— and/or —C(=O)—, with the proviso that two adjacent CH$_2$ groups cannot be replaced by heteroatoms, and/or
  b) one or more CH$_2$ groups may be replaced by —CH=CH— and/or —C≡C—, and/or
  c) one CH$_2$ group may be replaced by -Si(CH$_3$)$_2$—, cyclopropane-1,2-diyl, cyclobutane-1,3-diyl, cyclopentane-1,4-diyl, bicyclo[1.1.1]pentane-1,3-diyl or cyclohexane-1,4-diyl, and/or
  d) one or more H atoms may be replaced by F and/or CN;
  e) in the case of a straight-chain or branched alkyl radical containing asymmetrical carbon atoms, the asymmetrical carbon atoms either have —CH$_3$, —OCH$_3$, —CF$_3$, F, CN and/or C as substituents, or are incorporated into a 3- to 7-membered ring, in which, in addition, one or two non-adjacent CH$_2$ groups may be replaced by —O— and one CH$_2$ group may be replaced by —OC(=O)—;
$A^1$, $A^2$ and $A^3$ are identical or different and are
  phenylene-1,4-diyl, unsubstituted or monosubstituted or disubstituted by CN or F, phenylene-1,3-diyl, unsubstituted or monosubstituted or disubstituted by CN or F, cyclohexane-1,4-diyl, in which one or two H atoms may be replaced by CN and/or CH$_3$ and/or F, 1-cyclohexene-1,4-diyl, in which one H atom may be replaced by F, 1-alkyl-1-silacyclohexane-1,4-diyl, pyridine-2,5-diyl, unsubstituted or monosubstituted by F, pyrimidine-2,5-diyl, unsubstituted or monosubstituted by F, or thiophene-2,5-diyl;
M is undirected and is
  —OC(=O)—, —OCH$_2$—, —CH$_2$CH$_2$—, —OC(=O)CH$_2$CH$_2$—, —OCH$_2$CH$_2$CH$_2$—, —C≡—C—, —CH$_2$CH$_2$CH$_2$CH$_2$— a single bond;
a, b and c, independently of one another, are 0 or 1, with the proviso that the sum a+b+c is 1 or 2.

2. A liquid-crystal mixture comprising at least one compound of the formula (I) as claimed in claim 1.

3. A liquid-crystal mixture as claimed in claim 2, which is ferroelectric (chiral smectic).

4. A liquid-crystal mixture as claimed in claim 2, which is nematic.

5. A liquid-crystal mixture as claimed in claim 3, which comprises from 0.01 to 80% by weight of one or more compounds of the formula (I).

6. A ferroelectric switching and/or display device containing a ferroelectric liquid-crystal mixture as claimed in claim 3.

7. A ferroelectric switching and/or display device as claimed in claim 6, which is operated in $\tau V_{(min)}$ mode (inverse mode).

8. A ferroelectric switching and/or display device as claimed in claim 6, which contains active matrix elements.

* * * * *